United States Patent [19]

König et al.

[11] Patent Number: 4,656,223

[45] Date of Patent: Apr. 7, 1987

[54] PROCESS FOR THE PRODUCTION OF MODIFIED POLYISOCYANATES, THE COMPOUNDS OBTAINABLE BY THIS PROCESS AND THEIR USE IN POLYURETHANE LACQUERS

[75] Inventors: Klaus König, Leverkusen; Josef Pedain, Cologne; Helmut Woynar, Dormagen, all of Fed. Rep. of Germany

[73] Assignee: Bayer Aktiengesellschaft, Leverkusen, Fed. Rep. of Germany

[21] Appl. No.: 796,129

[22] Filed: Nov. 8, 1985

[30] Foreign Application Priority Data

Nov. 28, 1984 [DE] Fed. Rep. of Germany ....... 3443342

[51] Int. Cl.$^4$ ............................................. C08G 18/34
[52] U.S. Cl. ...................................... 524/871; 528/65; 528/66; 528/85
[58] Field of Search .................... 524/871; 528/65, 66, 528/85

[56] References Cited

U.S. PATENT DOCUMENTS 3,412,054 11/1968 Milligan et al. ...................... 524/591
4,447,571 5/1984 Dabi et al. ............................. 528/85

FOREIGN PATENT DOCUMENTS 2124640 2/1984 United Kingdom .

*Primary Examiner*—Maurice J. Welsh
*Attorney, Agent, or Firm*—Gene Harsh; Joseph C. Gil; Thomas W. Roy

[57] ABSTRACT

The present invention relates to a process for the production of modified organic polyisocyanates containing urethane, carboxylic acid anhydride and biuret groups by reacting excess quantities of organic diisocyanates with a modifying agent containing
(a) hydroxy carboxylic acids corresponding to the following general formula

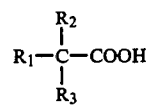

wherein $R_1$, $R_2$ and $R_3$ represent alkyl groups and at least one of which contains a hydroxyl group and, optionally,
(b) water wherein the molar ratio of (a) to (b) is about 0.02:1 to 1:0 and the ratio of mols of starting diisocyanate to mols of modifying agent (a) and (b) is about 3:1 to 24:1.

The present invention also relates to the modified polyisocyanates obtained by this process and to the use of these polyisocyantes, optionally blocked with blocking agents for isocyante groups, as the polyisocyanate component in polyisocyanate addition reactions.

9 Claims, No Drawings

PROCESS FOR THE PRODUCTION OF MODIFIED POLYISOCYANATES, THE COMPOUNDS OBTAINABLE BY THIS PROCESS AND THEIR USE IN POLYURETHANE LACQUERS

BACKGROUND OF THE INVENTION

1. Field of the Invention

This invention relates to a process for the production of new, modified polyisocyanates containing urethane, carboxylic acid anhydride and biuret groups by reacting simple starting diisocyanates with certain hydroxycarboxylic acids and, optionally, water; to the compounds obtainable by this process; and to their use, optionally in a form in which they have been blocked with blocking agents for isocyanate groups, as the polyisocyanate component in polyurethane lacquers.

2. Description of the Prior Art

Modified aliphatic diisocyanates, particularly based on hexamethylene diisocyanate, have acquired universal commercial significance for the production of light-stable, weatherproof lacquers with high gloss retention. Non-colored to faintly colored products are required for application in this field, particularly for clear and white-pigmented coatings. In addition, safe application presupposes a minimal content of monomeric diisocyanates which does not increase, even in the event of prolonged storage. Toxicological investigations have shown that safe processing is possible up to a maximal content of 0.7% of monomeric diisocyanate providing the safety measures normally adopted in the application of lacquers are observed. The above-mentioned limit has been accepted in the literature (cf. for example the pamphlet "PUR-Anstrichstoffe" of the Hauptverband der deutschen gewerblichen Berufsgenossenschaft and also "Polyurethane Report" of the Paintmakers Assoc.).

Over the years, many different forms of modification have been developed for the production of polyisocyanates of the type in question. For example, the following modification products of aliphatic diisocyanates have hitherto been successfully used in practice:

polyisocyanates containing uretdione groups produced by partial dimerization of diisocyanates in the presence of special catalysts, polyisocyanates containing isocyanurate groups produced by partial trimerization of diisocyanates in the presence of special catalysts, polyisocyanate mixtures containing both isocyanurate and also uretdione groups produced by partial trimerization and, at the same time, partial dimerization of diisocyanates in the presence of special catalysts which accelerate both the trimerization and the dimerization of isocyanate groups, polyisocyanates containing urethane groups produced by partial reaction of diisocyanates with polyols, normally with triols and polyisocyanates containing biuret groups produced by partial reaction of diisocyanates with a suitable biuretizing agent.

However, these modified lacquer-grade polyisocyanates which have been successfully used in practice are still in need of improvement in certain respects.

The uretdione and/or isocyanurate polyisocyanates are generally produced using special catalysts (for example phosphorus-containing compounds, tertiary amines or alkali metal carboxylates) which, to terminate the modification reaction at the required degree of modification, are generally destroyed by the addition of a terminator. In most cases, the resulting products (reaction products of the catalyst with the terminator) cannot be separated off from the end product which may cause clouding or unfavorable properties during the subsequent use of the product.

Although it is also possible to use catalysts which lose their effectiveness during the reaction as the temperature increases so that additional terminators are not required when compounds such as these are used, the exact amount of the catalysts required to achieve precisely defined conversions of isocyanate groups is difficult to determine. Further, the decomposition products of the catalysts remain in the product with the possible disadvantages mentioned above.

Although there is no need to use special catalysts in the production of urethane polyisocyanates, the known modified polyisocyanates solely containing urethane groups often show extremely high viscosities which seriously restrict their use (for example for the production of coatings) because heavy dilution with solvents is necessary to obtain suitable viscosities for processing. However, there is at present a distinct trend towards low-solvent or even solvent-free systems due both to industrial hygiene requirements and also to ecological and economic requirements.

State-of-the-art, lacquer-grade polyisocyanates containing biuret groups can be produced by many different methods in which it is also possible to adapt the viscosity of the modified polyisocyanates to the particular application envisaged. However, the modifying agents used for producing the biuret polyisocyanates (biuretizing agents such as water, compounds which give off water or various amines) are attended by special disadvantages which adversely affect either the method of production or the properties of the product.

If water is used as the biuretizing agent, large quantities of an organic solvent are required to convert the normally immiscible components, water and diisocyanate, into a homogeneous mixture suitable for carrying out the biuretizing process. Despite the use of these solvents, insoluble polyureas are often formed which can no longer be dissolved. Accordingly, in addition to the need to remove large quantities of solvents by distillation, an additional filtration step is often necessary.

Processes involving compounds which give off water (for example tertiary butanol) lead on the one hand to the loss of the biuretizing agent (isobutene) which has to be removed at considerable expense. On the other hand, temperatures above 160° C. have to be maintained for prolonged periods in these processes in order to achieve a complete reaction. However, due to the secondary reactions, temperatures as high as these leave the end products with poor color quality.

This also applies when amines are not formed in situ from isocyanates, but instead the excess diisocyanate is directly reacted with the corresponding diamine. However, the high reactivity of the amines to isocyanates unavoidably results in the formation of high molecular weight polyureas. In order to dissolve these polyureas to form biuret groups involves the application of high temperatures with the resulting deterioration in color quality and an increased occurrence of secondary products. Nor can the application of high temperatures be avoided by using special amines which do not form high-melting ureas with the diisocyanate or, where vapor-form amines are used, by avoiding the formation of solid ureas, because these reactions must of necessity be followed by equilibration reactions which only take place at high temperature. In addition to uretdiones and isocyanurates, carbodiimides and reaction products of carbodiimides also occur, adversely affecting the monomer stability of the end product.

Accordingly, an object of the present invention is to provide new modified polyisocyanates which satisfy all the demands made of high-quality lacquer-grade polyisocyanates, i.e. which show in particular excellent color quality and high monomer stability and which, in addition, can be produced easily under moderate conditions.

This object may be achieved by the process according to the invention which is described in detail in the following. In this process, certain starting diisocyanates are reacted with selected hydroxyalkane carboxylic acids or combinations thereof with water to form urethane, carboxylic acid anhydride and biuret groups.

Although the production of modified polyisocyanates by reaction of simple diisocyanates with aqueous solutions of water-soluble carboxylic acids is already known from DE-OS No. 3,228,721, the reaction of the starting diisocyanates with aqueous solutions of the acids mentioned therein leads to undesirable secondary products containing acyl urea groups formed via the intermediate stage of carboxylic acid amide groups. This not only deepens the color of the modified polyisocyanates according to the above-mentioned prior publication, but there is also the serious disadvantage that the modified polyisocyanates according to that prior publication and the secondary products containing acyl urea groups which are present in them are unstable and tend to split off the monomeric diisocyanates on which they are based. This disadvantage does not arise when the selected modifying agents essential to the invention are used. Instead, the process according to the invention which is described in detail hereinafter provides for the production of new, substantially colorless monomer-stable lacquer-grade polyisocyanates.

SUMMARY OF THE INVENTION

The present invention relates to a process for the production of modified organic polyisocyanates containing urethane, carboxylic acid anhydride and biuret groups by reacting excess quantities of organic diisocyanates with a modifying agent at temperatures in the range of about 20° to 160° C., optionally in the presence of water-miscible solvents and optionally with subsequent removal of excess unreacted starting diisocyanate and any other volatile constituents present from the reaction mixture by distillation and/or extraction, characterized in that the modifying agents used are
(a) hydroxycarboxylic acids corresponding to following general formula

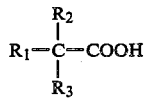

in which
  $R_1$ represents an optionally branched $C_1$–$C_8$ alkyl radical containing a primary or secondary alcoholic hydroxyl group as substituent,
  $R_2$ represents an optionally branched $C_1$–$C_8$ alkyl radical optionally containing a primary or secondary alcoholic hydroxyl group as substituent and
  $R_3$ represents an optionally branched, unsubstituted $C_1$–$C_{14}$ alkyl radical, the sum of the carbon atoms in the radicals $R_1$, $R_2$ and $R_3$ amounting to between 3 and 20,
and, optionally,
(b) water, the molar ratio of (a) to (b) being about 0.02:1 to 1:0 and the total quantity of midifying agents (a) and (b) being present in such an amount that the ratio of moles of starting diisocyanate to total moles of modifying agents (a) and (b) is about 3:1 to 24:1.

The present invention also relates to the modified polyisocyanates obtained by this process and to the use of these polyisocyanates, optionally blocked with blocking agents for isocyanate groups, as the polyisocyanate component in polyisocyanate addition reactions.

DETAILED DESCRIPTION OF THE INVENTION

Starting diisocyanates suitable for the process according to the invention are any diisocyanates containing aliphatically bound isocyanate groups and having a molecular weight in the range from 140 to 300. The inert residues linking the isocyanate groups of these diisocyanates are preferably aliphatic hydrocarbon residues which may optionally contain ester groups as substituents or in the main chain. Examples of the diisocyanates in question are 1,4-diisocyanatobutane, 1,5-diisocyanatopentane, 1,6-diisocyanatohexane, 1,8-diisocyanatooctane, 1,10-diisocyanatodecane, isomer mixtures of 2,2,4-trimethyl- and 2,4,4-trimethyl-1,6-diisocyanatohexane, 2-methyl-1,5-diisocyanatopentane, 2,2-dimethyldiisocyanatopentane, 6-isocyanatohexanoic acid-(2-isocyanatoethyl)-ester, 2,6-diisocyanatohexanoic acid methyl ester. Basically, it is also possible to use the aliphatic diisocyanates mentioned by way of example in admixture with cycloaliphatic diisocyanates such as, for example, 4,4'-diisocyanatodicyclohexylmethane or 1-isocyanato-3-isocyanatomethyl-3,5,5-trimethyl-cyclohexane, although this is less preferred. It is particularly preferred to use 1,6-diisocyanatohexane as the sole starting diisocyanate in the process according to the invention.

In the context of the invention, "modifying agents" are understood to be isocyanate-reactive compounds which react with the starting diisocyanates to form urethane, carboxylic acid anhydride and biuret groups. The modifying agents essential to the invention are (a) certain hydroxycarboxylic acids or combinations thereof with (b) water.

The hydroxycarboxylic acids (a) suitable for the process according to the invention correspond to the following general formula

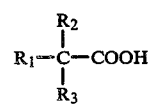

wherein $R_1$, $R_2$ and $R_3$ are as already defined.

It is preferred to use hydroxycarboxylic acids corresponding to the above general formula in which
  $R_1$ is a hydroxymethyl radical,
  $R_2$ is a hydroxymethyl, methyl or ethyl radical and
  $R_3$ is an optionally branched $C_1$–$C_4$ alkyl radical.

Typical examples of hydroxycarboxylic acids such as these include 2-hydroxymethyl-2-methyl pentanoic acid, 2-hydroxymethyl-2-ethylhexanoic acid, 3-hydroxy pivalic acid and 2,2-dimethylol propionic acid. The last two acids are preferably used, 3-hydroxy pivalic acid being particularly preferred.

In a first variant of the process according to the invention, the hydroxycarboxylic acids mentioned by way of example may be used as sole modifying agent. In a second variant of the process, the hydroxycarboxylic acids according to the invention are used in combination with water, so that the combination of hydroxycarboxylic acid and water represents the modifying agent. In general, the modifying agents (a) and optionally (b) are used in a molar ratio of hydroxycarboxylic acid to water of about 0.02:1 to 1:0 and preferably about 0.05:1 to 1:0, the ratio of the molar quantity of starting diisocyanate to the total molar quantity of the modifying agent being about 3:1 to 24:1 and preferably about 5:1 to 15:1.

It is of course possible in principle to use other modifying agents known per se in addition to the modifying agents used in accordance with the invention, although this is less preferred.

It can be of advantage, particularly where water is used, to carry out the process according to the invention in the presence of a solvent which is miscible with water at least within certain limits and which is inert to isocyanate, acid and hydroxyl groups under the reaction conditions applied. Examples of solvents which may optionally be used are ethers such as diisopropyl ether, ethylene glycol dimethyl ether, diethylene glycol dimethyl ether, 1,4-dioxane, tetrahydrofuran and 1,2-dimethoxypropane; esters such as butyrolactone, ethylene glycol carbonate and propylene glycol carbonate; ether esters such as methoxyethyl acetate, ethoxyethyl acetate, 1-methoxypropyl-2-acetate, 2-methoxypropyl-1-acetate, 1-ethoxypropyl-2-acetate and 2-ethoxypropyl-1-acetate; ketones such as acetone and methylethyl ketone; nitriles such as acetonitrile, propionitrile and methoxypropionitrile; sulfones such as sulfolan, dimethyl sulfone and diethyl sulfone; phosphoric acid esters such as triethyl phosphate and trimethyl phosphate; and mixtures of these solvents.

Less preferred solvents include tetramethyl urea, N-methylpyrrolidone, dimethyl formamide, dimethyl acetamide.

The process is carried out at temperatures of about 20° to 160° C. and preferably at temperatures of about 50° to 140° C. The process is generally carried out under normal pressure, although it may of course also be carried out under pressures of about 1 to 30 bars and preferably under pressures of about 1 to 5 bars, particularly when water and/or low-boiling solvents are used.

The hydroxyl groups of the modifying agents (a) react with a portion of the isocyanate groups in the starting diisocyanate to form urethane groups and the water which is eliminated from the conversion of carboxylic acid groups to carboxylic acid anhydride groups reacts with an additional portion of the isocyanate groups to form biurets. However, the exact reaction mechanism remains largely unresolved. These reactions surprisingly take place under extremely mild conditions, for example at temperatures of the order of 80° C.; whereas, the direct reaction of diisocyanates with water in the absence of the modifying agents (a) essential to the invention is known to require considerably more severe reaction conditions. In cases where modifying agents (a) are used in combination with the modifying agent (b), namely water, the modifying agents (a) develop a catalytic effect with respect to biuretization through reaction of a portion of the isocyanate groups with water, and the formation of urethane and carboxylic acid anhydride groups through reaction of additional isocyanate groups with component (a), so that the diisocyanate-water reaction may be carried out at distinctly lower temperatures than in the absence of the hydroxycarboxylic acids (a). When combinations of the individual components (a) and (b) which predominantly contain water are used as the modifying agents, the polyisocyanates formed primarily contain biuret groups and only small quantities of urethane and carboxylic acid anhydride groups. Basically, the particular concentration of urethane, carboxylic acid anhydride and biuret groups in the end products of the process according to the invention depends primarily on the ratio of the particular modifying agents (a) and (b).

The process according to the invention is carried out, for example, as follows:

The diisocyanate used is introduced at room temperature or elevated temperature into a stirrer-equipped reactor optionally provided with an instrument for measuring the carbon dioxide formed.

If a hydroxycarboxylic acid is used as the sole modifying agent, it is introduced into the diisocyanate at room temperature, provided it is liquid at room temperature, over a period of about 30 minutes resulting in the onset of an exothermic reaction with evolution of $CO_2$, this reaction being continued at a reasonable velocity by heating to 60°–80° C. The deceleration which begins towards the end of the reaction is counteracted by heating to 100°–120° C. The time required for the reaction as a whole is generally about 1 to 12 hours and preferably about 2 to 8 hours.

Hydroxycarboxylic acids which are solid at room temperature are generally added to the diisocyanate in that form, the diisocyanate advantageously being introduced beforehand at elevated temperature (80°–120° C.). The acid is added commensurately with the progress of the reaction as determined, for example, by the evolution of $CO_2$.

If a hydroxycarboxylic acid is used in combination with water as the modifying agent, it is of advantage in any event initially to introduce the diisocyanate at elevated temperature. In this case, it is also of particular advantage to use a solvent as solution promoter between water and diisocyanate, otherwise difficultly soluble precipitates of polyurea can form in the reaction mixture. In addition, water can be entrained by escaping carbon dioxide, condensing on the upper parts of the reaction vessel or entering the off-gases and thus being removed from the reaction. These uncontrolled losses of water can be avoided by adding a solvent with a suitable boiling point which is miscible with water at least within certain limits. However, the quantity of solvent required is distinctly smaller than in processes using water as sole modifying agent.

All or a portion of the solvent, optionally used, may be initially introduced with the diisocyanate or all or a portion may be added to the diisocyanate with the hydroxycarboxylic acid or the water optionally used.

In cases where combinations of hydroxycarboxylic acids and water are used as modifying agents, the two individual components may be used either separately or in the form of an aqueous solution of the hydroxycarboxylic acid. When water and/or solvents are used, it can be preferable to work under excess pressure in order to avoid losses of those components. The maximum pressure prevailing during the reaction is advantageously limited to about 5 bars by suitable measures, for example by a pressure retaining valve, because standard technical equipment can be used without difficulty up to that pressure. The reaction may of course also be carried out under higher pressures, for example under the full natural pressure of the carbon dioxide formed during the reaction, in which case pressures of up to about 20 bars can occur according to the temperature profile and the extent to which the reactor is filled. In cases such as these, however, special high-pressure apparatus are required.

As already mentioned, the ratio of NCO groups to acid and water may be varied within wide limits. It determines the distribution of oligomers in the resulting polyisocyanate and, hence, crucial properties of the product, for example its isocyanate content and viscosity.

In addition, it is possible through the type and quantity of hydroxycarboxylic acids used to introduce different groups into the modified polyisocyanates which enable the properties of the end product to be adapted to the applications envisaged. On completion of the reaction, excess diisocyanate is generally removed from the reaction mixture by distillation. If a solvent has been used, it may be separated from the diisocyanate used by distillation, providing it boils at a lower temperature than the diisocyanate. However, it is of greater advantage to separate the solvent together with the diisocyanate if the diisocyanate and the solvent are to be reused.

In principle, it is also possible, although less preferred, to separate the excess diisocyanate from the polyisocyanate formed by extraction, for example with n-hexane, for example after removal of the solvent used, if any.

The process may also be carried out in a continuous manner. In this case, for example, diisocyanate and hydroxycarboxylic acid are introduced separately or in admixture, optionally together with water and/or a solvent, into the first of 4-6 stirrer-equipped reactors arranged one behind the other in a cascade in such a way that the overall residence time in the reactor cascade is between about 2 and 8 hours. In this connection, the temperature prevailing in each reactor of the cascade may be in the range from about 100° to 120° C. or may rise from about 20° to 140° C. and, preferably, from about 40° to 120° C. in the individual reactors. Depending on the boiling points of the diisocyanate and the solvent used, if any, the reaction mixture may initially be passed through a continuous distillation column to separate the solvent and subsequently the modified polyisocyanate may be freed from excess diisocyanate by thin-layer distillation or by extraction. Alternatively, the polyisocyanate may first be freed from excess diisocyanate and solvent by thin-layer evaporation and subsequently the diisocyanate and solvent may be separated by distillation. However, it is of advantage to separate the solvent together with the diisocyanate and to return the distillate to the process without any further working up. In general, the products obtained by the process according to the invention are freed from monomeric starting diisocyanates to a residual content of at most 0.7% by weight.

The polyisocyanates according to the invention produced by the process according to the invention are distinguished by high color quality and also by high stability in storage and are substantially free from secondary products.

When the modified polyisocyanates are used in combination with polyhydroxyl compounds, free acid groups (which can be of advantage to the adhesion to metals of coatings produced from these products) are formed from the acid anhydride groups present in the modified polyisocyanates. These anhydride groups may also be used—after blocking of the isocyanate groups of the polyisocyanate with a suitable blocking agent such as $\epsilon$-caprolactam, phenol, malonic acid diethyl ester or butanone oxime—to produce acid groups by hydrolysis, the acid groups thus produced subsequently serving as an ionic center for the production of water-soluble or water-dispersible PU systems. In principle, the products obtained by the process according to the invention may be used for any applications for which the lacquer-grade polyisocyanates have previously been used. The products obtained by the process according to the invention are particularly suitable for use as the polyisocyanate component in the polyisocyanate addition process by reaction with compounds containing isocyanate-reactive groups, preferably for the formation of polyurethane lacquers by reaction with compounds containing hydroxyl groups. For this purpose the polyisocyanates of the invention may also be used in blocked form i.e. as reaction products with blocking agents as those exemplified thereinbefore.

The invention is illustrated by the following examples in which all the percentages quoted are percentages by weight.

EXAMPLES

EXAMPLE 1

In a 6 liter four-necked flask equipped with a contact thermometer, stirrer and reflux condenser, 472 g (4 moles) of solid hydroxy pivalic acid (2-hydroxymethyl-2,2-dimethylacetic acid) were added at 20° C. to 4032 g (24 moles) of 1,6-diisocyanatohexane. The reaction mixture was then heated to a final temperature of 120° C. as quickly as permitted by the evolution of gas which began at an early stage (about 2 hours). After the temperature of 120° C. had been reached, the reaction mixture was stirred for about 1 hour until the evolution of gas was complete. In all, 49.5 l of $CO_2$ (corr.) were released. The crude polyisocyanate obtained (NCO content 34.5%) was freed from excess 1,6-diisocyanatohexane by thin-layer distillation twice in a Leybold-Heraeus KDT 6 short-path evaporator. In the first step, most of the diisocyanate was distilled off at a jacket temperature of 130°-140° C. and at a throughput of 4-6 kg/h. In the second step, the remainder of the diisocyanate was removed at the same jacket temperature, but at a lower throughput of about 3-4 kg/h. 2058 g of a modified polyisocyanate having the following properties were obtained:

NCO-content: 17.6%
Viscosity at 23° C.: 13900 mPas
APHA color index (DIN 53 409): 20
Monomeric diisocyanate content: 0.03%

The IR spectrum reveals the presence of biuret groups (edge at 1700 cm$^{-1}$), urethane groups (edge at 1725 cm$^{-1}$), uretdione groups (weak shoulder at 1775 cm$^{-1}$) and anhydride groups (edge at 1820 cm$^{-1}$).

EXAMPLE 2

4032 g (24 moles) of 1,6-diisocyanatohexane were introduced at 120° C. into a stirrer-equipped apparatus of the type described in Example 1. 268 g (2 moles) of solid dimethylol propionic acid were introduced into the diisocyanate over a period of 1 h. After the addition, the mixture was stirred at 120° C. for 1 h. In all, 28 l of $CO_2$ (corr.) were released during the reaction. After thin-layer evaporation of the excess diisocyanate, 1476 g of a modified polyisocyanate having the following properties were obtained:
  NCO-content: 18.4%
  Viscosity at 23° C.: 6300 mPas
  APHA color index (DIN 54 409): 50
  Monomeric diisocyanate content: 0.03%

EXAMPLE 3

4200 g (25 moles) of 1,6-diisocyanatohexane and 300 g of phosphoric acid trimethyl ester were introduced into the apparatus described in Example 1 and heated to 100° C. A solution of 59 g (0.5 mole) of hydroxy pivalic acid in 27 g (1.5 moles) of water were then added dropwise over a period of 2 hours. The acid-water mixture was kept at a temperature of at least 50° C. to enable it to be added in liquid form. After the addition, the mixture was stirred at 120° C. for 1 h and a total of 39.2 l (corr.) of $CO_2$ was released. On completion of the reaction, the excess diisocyanate was removed together with the phosphoric acid trimethyl ester by thin-layer distillation. (After the addition of fresh 1,6-diisocyanatohexane, this distillate may be used without further purification for following runs.)

860 g of a modified polyisocyanate having the following properties were obtained as sump product:
  NCO-content: 22.8%
  Viscosity at 23° C.: 5600 mPas
  APHA color index: 20
  Monomeric diisocyanate content: <0.07 %

EXAMPLE 4

4536 g (27 moles) of 1,6-diisocyanatohexane and 600 ml of dioxane were reacted as in Example 3 with a mixture of 80.4 g (0.6 mole) of dimethylol propionic acid and 70.2 g (3.0 moles) of water. In contrast to Example 3, most of the low-boiling solvent was separated off by ordinary distillation before the thin-layer distillation step. 1590 g of a modified polyisocyanate having the following properties were obtained:
  NCO-content: 21.6%
  Viscosity at 23° C.: 9800 mPas
  APHA color index: 30
  Monomeric diisocyanate content: <0.03%

EXAMPLE 5

4200 g (25 moles) of 1,6-diisocyanatohexane and 350 g of phosphoric acid trimethyl ester were reacted as in Example 3 with a solution of 36 g (2 moles) of water and 11.8 g (0.1 mole) of hydroxy pivalic acid. 906 g of a modified polyisocyanate having the following properties were obtained:
  NCO-content: 22.9%
  Viscosity at 23° C.: 1580 mPas
  APHA color index: 30
  Monomeric diisocyanate content: <0.03%

EXAMPLE 6

4200 g (20 moles) of 1,6-diisocyanatoltrimethyl hexane (technical isomer mixture of the 2,2,4- and 2,4,4-trimethyl-substituted compounds) and 500 ml of 1,2-dimethoxyethane were reacted as in Example 3 with 27 g (1.5 moles) of water and 17.4 g (0.1 mole) of 2-ethyl-2-hydroxymethylhexanoic acid. The water and acid being added separately, but at the same time to the diisocyanate. 895 g of a modified diisocyanate having the following properties were obtained:
  NCO-content: 18.2%
  Viscosity at 23° C.: 13600 mPas
  APHA color index: 20
  Monomeric diisocyanate content: <0.07%

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of modified organic polyisocyanates containing urethane, carboxylic acid anhydride and biuret groups which comprises reacting excess quantities of an organic diisocyanate with a modifying agent at a temperature of about 20° to 160° C., said modifying agent comprising (a) a hydroxycarboxylic acid corresponding to the formula

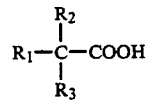

wherein
  $R_1$ represents an optionally branched $C_1$–$C_8$ alkyl radical containing a primary or secondary alcoholic hydroxyl group as substituent,
  $R_2$ represents an optionally branched $C_1$–$C_8$ alkyl radical optionally containing a primary or secondary alcoholic hydroxyl group as substituent and
  $R_3$ represents an optionally branched, unsubstituted $C_1$–$C_{14}$ alkyl radical,
  the sum of the carbon atoms in the radicals $R_1$, $R_2$ and $R_3$ amounting to between 3 and 20
and, optionally
(b) water, wherein the molar ratio of (a) to (b) is about 0.02:1 to 1:0 and the ratio of moles of starting diisocyanate to total moles of modifying agent (a) and (b) is between about 3:1 and 24:1.

2. The process of claim 1 wherein (a) is monohydroxy pivalic acid or 2,2-dimethylol propionic acid.

3. The process of claim 1 wherein said organic diisocyanate is 1,6-diisocyanatohexane.

4. The process of claim 1 wherein the reaction is carried out at a temperature of about 50° to 140° C.

5. The process of claim 1 wherein the modifying agent (a) and (b) are used in a molar ratio of about 0.05:1 to 1:0 and the molar ratio of starting diisocyanate to modifying agent (a) and (b) is between about 5:1 and 15:1.

6. The process of claim 1 wherein the reaction is carried out in the presence of a solvent which is miscible with water at least within certain limits and which is inert to isocyanate, acid and hydroxyl groups under the reaction conditions applied.

7. The modified polyisocyanates obtained by the process of claim 1.

8. A process for the production of a polyisocyanate addition product which comprises reacting (a) the modified polyisocyanates of claim 7 optionally in blocked form with a
(b) compound containing isocyanate-reactive groups.

9. The process of claim 8 wherein said polyisocyanate addition product is a polyurethane and said isocyanate-reactive groups comprise hydroxyl groups.

* * * * *